United States Patent
Fisher

(10) Patent No.: US 10,806,676 B2
(45) Date of Patent: Oct. 20, 2020

(54) RELAY TRAY

(71) Applicant: Omnicell, Inc., Mountain View, CA (US)

(72) Inventor: Herbert Lawson Fisher, Portola Valley, CA (US)

(73) Assignee: Omnicell, Inc., Mountain View, CA (US)

( * ) Notice: Subject to any disclaimer, the term of this patent is extended or adjusted under 35 U.S.C. 154(b) by 222 days.

(21) Appl. No.: 15/884,073

(22) Filed: Jan. 30, 2018

(65) Prior Publication Data

US 2019/0231644 A1     Aug. 1, 2019

(51) Int. Cl.
| | |
|---|---|
| *A61J 7/00* | (2006.01) |
| *G16H 20/13* | (2018.01) |
| *G05B 15/02* | (2006.01) |
| *A61G 12/00* | (2006.01) |

(52) U.S. Cl.
CPC .......... *A61J 7/0069* (2013.01); *A61G 12/001* (2013.01); *A61J 7/0084* (2013.01); *G05B 15/02* (2013.01); *G16H 20/13* (2018.01); *A61J 2205/60* (2013.01)

(58) Field of Classification Search
CPC . A61J 7/0084; G07F 17/0092; G06F 19/3462
See application file for complete search history.

(56) References Cited

U.S. PATENT DOCUMENTS

| | | |
|---|---|---|
| 5,190,185 A | 3/1993 | Blechl |
| 5,377,864 A | 1/1995 | Blechl et al. |
| 5,615,625 A | 4/1997 | Netshisaulu et al. |
| 5,745,366 A | 4/1998 | Higham et al. |

(Continued)

FOREIGN PATENT DOCUMENTS

| | | |
|---|---|---|
| DE | 102004037365 | 12/2011 |
| JP | 2003027797 A | 1/2003 |

(Continued)

OTHER PUBLICATIONS

U.S. Appl. No. 15/019,802 received a Final Office Action dated Jun. 1, 2018, 18 pages.

(Continued)

*Primary Examiner* — Timothy R Waggoner
(74) *Attorney, Agent, or Firm* — Kilpatrick Townsend & Stockton LLP

(57) ABSTRACT

A relay tray for securely transporting items includes a lockable transportable container for holding items to be transported, and an electronic controller including a processor. The relay tray receives electric power through a power interface, and includes a commination interface through which the controller can communicate electronically. The relay tray includes a mechanism operable under control of the controller to make items in the locked container accessible in response to communications received via the communication interface, the mechanism operable by the controller only when power is being received through the power interface. In some implementations, the power interface includes four electrical contacts on an outside surface of the container for receiving power and a rectifier that produces voltage of a polarity suitable for powering the controller. The power interface may function as the communication interface.

30 Claims, 10 Drawing Sheets

(56) References Cited

U.S. PATENT DOCUMENTS

| | | | |
|---|---|---|---|
| 5,805,455 A | 9/1998 | Lipps | |
| 5,805,456 A | 9/1998 | Higham et al. | |
| 5,905,653 A * | 5/1999 | Higham | G07F 17/0092 |
| | | | 312/215 |
| 5,927,540 A | 7/1999 | Godlewski | |
| 6,011,999 A | 1/2000 | Holmes | |
| 6,039,467 A | 3/2000 | Holmes | |
| 6,040,771 A | 3/2000 | Kim | |
| 6,116,461 A * | 9/2000 | Broadfield | A61G 12/001 |
| | | | 206/443 |
| 6,151,536 A | 11/2000 | Arnold et al. | |
| 6,170,929 B1 | 1/2001 | Wilson et al. | |
| 6,272,394 B1 | 8/2001 | Lipps | |
| 6,385,505 B1 | 5/2002 | Lipps | |
| 6,472,973 B1 | 10/2002 | Harold et al. | |
| 6,609,047 B1 | 8/2003 | Lipps | |
| 6,640,159 B2 | 10/2003 | Holmes et al. | |
| 6,760,643 B2 | 7/2004 | Lipps | |
| 6,761,578 B1 * | 7/2004 | Stavely | H01R 33/96 |
| | | | 200/5 D |
| 6,975,922 B2 | 12/2005 | Duncan et al. | |
| 7,006,893 B2 | 2/2006 | Hart et al. | |
| 7,080,755 B2 * | 7/2006 | Handfield | A61J 7/0076 |
| | | | 221/13 |
| 7,348,884 B2 | 3/2008 | Higham | |
| 7,571,024 B2 | 8/2009 | Duncan et al. | |
| 7,654,261 B1 | 2/2010 | Rockhold | |
| 7,675,421 B2 | 3/2010 | Higham | |
| 7,734,372 B2 | 6/2010 | Shoenfeld | |
| 7,835,819 B2 | 11/2010 | Duncan et al. | |
| 8,027,749 B2 | 9/2011 | Vahlberg et al. | |
| 8,073,563 B2 | 12/2011 | Vahlberg et al. | |
| 8,126,590 B2 | 2/2012 | Vahlberg et al. | |
| 8,131,397 B2 | 3/2012 | Vahlberg et al. | |
| 8,140,186 B2 | 3/2012 | Vahlberg et al. | |
| 8,155,786 B2 | 4/2012 | Vahlberg et al. | |
| 8,749,382 B2 | 6/2014 | Sterzinger et al. | |
| 9,418,495 B2 | 8/2016 | Mackin et al. | |
| 9,697,663 B2 | 7/2017 | Johnson et al. | |
| 10,186,100 B2 | 1/2019 | Foot et al. | |
| 2004/0054436 A1 | 3/2004 | Haitin et al. | |
| 2004/0111179 A1 | 6/2004 | Broadfield et al. | |
| 2004/0215981 A1 * | 10/2004 | Ricciardi | G06Q 50/24 |
| | | | 726/27 |
| 2005/0232747 A1 | 10/2005 | Brackmann et al. | |
| 2006/0080819 A1 | 4/2006 | McAllister | |
| 2007/0018791 A1 | 1/2007 | Johnson et al. | |
| 2007/0194526 A1 | 8/2007 | Randall | |
| 2008/0112300 A1 | 5/2008 | Kumhyr et al. | |
| 2008/0319577 A1 | 12/2008 | Vahlberg et al. | |
| 2008/0319579 A1 | 12/2008 | Vahlberg et al. | |
| 2008/0319789 A1 | 12/2008 | Vahlberg et al. | |
| 2008/0319790 A1 | 12/2008 | Vahlberg et al. | |
| 2009/0015400 A1 | 1/2009 | Breed | |
| 2009/0108016 A1 * | 4/2009 | Brown | A61J 7/0084 |
| | | | 221/28 |
| 2009/0328171 A1 | 12/2009 | Bayus et al. | |
| 2010/0042437 A1 | 2/2010 | Levy et al. | |
| 2012/0158606 A1 | 6/2012 | Moudy | |
| 2012/0229253 A1 | 9/2012 | Kolar et al. | |
| 2013/0006652 A1 | 1/2013 | Vahlberg et al. | |
| 2013/0187774 A1 | 7/2013 | Muecke et al. | |
| 2014/0033774 A1 | 2/2014 | Ofchus et al. | |
| 2014/0128023 A1 | 5/2014 | Guerra | |
| 2014/0187261 A1 | 7/2014 | Lee et al. | |
| 2014/0340191 A1 | 11/2014 | Clark et al. | |
| 2015/0005934 A1 * | 1/2015 | Bell | G06F 19/3462 |
| | | | 700/237 |
| 2015/0077221 A1 | 3/2015 | Peters et al. | |
| 2016/0023636 A1 | 1/2016 | Keating et al. | |
| 2016/0155281 A1 | 6/2016 | O'Toole et al. | |
| 2016/0253860 A1 | 9/2016 | Wilson et al. | |
| 2016/0343187 A1 | 11/2016 | Trani | |
| 2017/0113955 A1 | 4/2017 | Reilly et al. | |
| 2017/0188199 A1 | 6/2017 | Ashley, Jr. et al. | |
| 2017/0228951 A1 | 8/2017 | Foot et al. | |
| 2018/0359343 A1 | 12/2018 | Lee et al. | |
| 2019/0003205 A1 | 1/2019 | Zastrow et al. | |

FOREIGN PATENT DOCUMENTS

| | | |
|---|---|---|
| JP | 2006336254 A | 12/2006 |
| JP | 4557807 | 10/2010 |
| WO | 2010106552 | 9/2010 |
| WO | 2010151903 | 12/2010 |
| WO | 2014065196 A1 | 5/2014 |
| WO | 2017139188 A1 | 8/2017 |

OTHER PUBLICATIONS

BR1120180161829 received an Office Action dated Jun. 4, 2019, 11 pages.

AU2017216982 received a First Examination Report dated Jul. 16, 2019, 5 pages.

JP Application No. 2013-539998 received an Office Action dated Jun. 4, 2019, 5 pages.

PCT/US2019/015199 received an International Search Report and Written Opinion dated May 30, 2019, 13 pages.

PCT/US2019/015199 received an Invitation to Pay Additional Fees dated Apr. 4, 2019, 2 pages.

International Patent Application No. PCT/US2017/016374 International Search Report and Written Opinion dated Jun. 12, 2017 18 pages.

International Patent Application No. PCT/US2017/016374, Invitation to Pay Additional Fees and Partial Search report dated Apr. 3, 2017, 2 pages.

Chipworks, "Apple iPhone 5—the RF" [May 1, 2015 archive retrieved from the internet Apr. 26, 2016: https://web.archive.org/web/20150501080502/http://www.chipworks.com/en/technical-competitive-analysis/resources/blog//apple-iphone-5-the-rf?lang=en&Itemid=815>], 7 pages.

Cisco, "Cisco 2700 Series Wireless Location Appliance Deployment Guide", [Apr. 23, 2015 archive retrieved from the internet Apr. 26, 2016: https://web.archive.org/web/20150423203946/http://www.cisco.com/c/en/us/td/docs/wireless/technology/location/deployment/guide/depgd.html>], 19 pages.

Digikey Electronics, "Bluetooth Goes Ultra-Low-Power", [Jan. 28, 2016 archive retrieved from the internet Apr. 26, 2016: https://web.archive.org/web/20160128092552/http://www.digikey.com/en/articles/techzone/2011/dec/bluetooth-goes-ultra-low-power], 6 pages.

Digikey Electronics, "Comparing Low-Power Wireless Technologies", [Aug. 21, 2015 archive retrieved from the internet Apr. 26, 2016: https://web.archive.org/web/20159821095244/http://www.digikey.com/en/articles/techzone/2011/aug/comparing-low-power-wireless-technologies>], 11 pages.

Electrical Engineering Stack Exchange, "Bluetooth vs. Bluetooth Smart (Low Energy)", [Sep. 10, 2015 archive retrieved from the internet Apr. 26, 2016: https://web.archive.org/web/20150910054027/http://electronics.stackexchange.com/questions/53583/bluetooth-vs-bluetooth-smart-low-energy>], 2 pages.

Find my car smarter, "Find My Car Smarter", [Oct. 18, 2015 archive retrieved from the internet Apr. 26, 2016: https://web.archive.org/web/20151018145721/http://findmycarsmarter.com/setup—usage.html>], 1 page.

Trifunovic, et al., "Slicing the Battery Pie: Fair and Efficient Energy Usage in Device-to-Device Communication via Role Switching", Sep. 30, 2013, 6 pages.

Wikipedia, "Electronic article surveillance", [Dec. 17, 2015 archive retrieved from the internet Apr. 26, 2016: https://web.archive.org/web/20151217225518/https://en.wikipedia.org/wiki/Electronic_article_surveillance],6 pages.

Wikipedia, "Geo-fence", [Jan. 20, 2016 archive retrieved from the internet Apr. 26, 2016: <https://web.archive.org/web/20160120124728/https://en.wikipedia.org/wiki/Geo-fence>], 2 pages.

Wikipedia, "Near Field Communication", [Feb. 7, 2016 archive retrieved from the internet Apr. 26, 2016: https://web.archive.org/web/20160207043254/https://en.wikipedia.org/wiki/Near_field_communication], 11 pages.

(56) References Cited

OTHER PUBLICATIONS

Wikipedia, "Real-time locating system", [Nov. 6, 2015 archive retrieved from the internet Apr. 26, 2016: https://web.archive.org/web/20151108213536/http://en.wikipedia.org/wiki/Real-time_locating_system], 8 pages.
Unknown, "Open Dots Technology Specification," [Maintained by: Open Dots Alliance © 2014, Rev. 1.2, accessed from the internet: http://opendotsalliance.org/wp-content/uploads/2014/10/OpenDotsSpecifications1dot2.pdf], 8 pages.
U.S. Appl. No. 15/019,802 received a Non-Final Office Action dated Oct. 19, 2017, 15 pages.
U.S. Appl. No. 16/216,813 received a Non-Final Office Action dated Jan. 25, 2019, 13 pages.
PCT/US2017/016374 received an International Preliminary Report on Patentability dated Aug. 23, 2018, 14 pages.
BR1120180161829 received an Office Action dated Nov. 12, 2019, 7 pages.
EP17750595.5 received an Extended European Search Report dated Oct. 14, 2019, 8 pages.
AU2017216982 received a Second Examination report dated Mar. 27, 2020, 3 pages.

\* cited by examiner

RELAY TRAY

BACKGROUND OF THE INVENTION

Many industries rely on the accurate inventory and dispensing of secure items. For example, in a hospital setting, medications are often stored in lockable cabinets in communication with a computer system that tracks inventories of the medications. The cabinets, or individual compartments within the cabinets, may be opened only under control of the computer system. For example, a nurse or other health care worker may provide authentication credentials to the computer system and indicate that a particular medication is needed for a particular patient. The computer system can then open the compartment in which the particular medication is stored, so that the health care worker can retrieve it and administer it to the patient. The computer system can adjust its tracking records accordingly. Such systems help ensure that the correct medication is dispensed for the correct patient, that controlled substances are properly secured and tracked, and that detailed inventory records are kept.

Various dispensing cabinets and carts have been developed to assist in the management of medications and other items. However, improvements are still desired in the dispensing and tracking of items, especially during transport of items such as medications from one location to another within a facility.

Similar requirements for secure transport and tracking of items arise in other industries, for example transport of cash or other valuables in a banking or business environment.

BRIEF SUMMARY OF THE INVENTION

According to one aspect, a relay tray for securely transporting items comprises a lockable transportable container for holding items to be transported, an electronic controller including a processor, a power interface though which the relay tray can receive electric power, a communication interface through which the controller can communicate electronically, and a mechanism operable under control of the controller to make items in the locked container accessible in response to communications received via the communication interface. The mechanism is operable by the controller only when power is being received through the power interface. In some embodiments, the mechanism is a lock operable by the controller to unlock a compartment of the relay tray. In some embodiments, the controller further comprises a nonvolatile memory storing a listing of an item or items in the relay tray. In some embodiments, the relay tray further comprises a plurality of compartments within the container, wherein the compartments are individually lockable, and are individually openable under control of the controller in response to communications received via the communication interface. In some embodiments, the relay tray further comprises a plurality of lights associated respectively with at least some of the compartments, the lights being individually operable under control of the controller. In some embodiments, the power interface also serves as the communication interface, and the controller is configured to extract incoming communications signals from the power interface, and to impose outgoing communication signals on the power interface. In some embodiments, the power interface comprises four electrical contacts on an outside surface of the container for receiving electric power connections; and a rectifier that receives power from the four electrical contacts and produces voltage of a polarity suitable for powering the controller. In some embodiments, the four contacts are positioned at the vertices and center of an equilateral triangle. In some embodiments, the four contacts also serve as the communications interface, and the controller is configured to extract communications signals imposed on the contacts in addition to the power voltages. In some embodiments, the relay tray is configured to receive DC power, and the rectifier produces DC voltage of a polarity suitable for powering the controller. In some embodiments, the relay tray is configured to receive AC power, and the rectifier produces rectified AC voltage. In some embodiments, the communications interface is a short range wireless communications interface. In some embodiments, the communications interface is a wired communications interface. In some embodiments, the power interface comprises a coil that receives power by inductive coupling. In some embodiments, the relay tray includes one or more electromechanical actuators; and the relay tray does not include a battery powering operation of any of the one or more electromechanical actuators. In some embodiments, the mechanism comprises one or more electromechanical dispensers configured to dispense items under control of the controller. In some embodiments, items are dispensed in response to communications received via the communication interface. The relay tray may also be openable by a key. In some embodiments, the relay further comprises a nonvolatile display on an outside surface of the container. In some embodiments, the relay tray stores a hashed identifier of a person for whom an item in the relay tray is intended. In some embodiments, the relay tray further comprises a passive externally-excitable memory device storing an identifier of the relay tray. In some embodiments, the controller is configured to authenticate the source of the communications received via the communication interface before making an item in the locked container accessible. In some embodiments, the relay tray further comprises a low power wireless beacon receiver, and during transport of the relay tray, the controller records the detection of any beacon signals detected by the low power wireless beacon receiver.

According to another aspect, a charging and communication surface for electronic devices comprises a plurality of first linear electrical conductors with exposed metal surfaces. The first linear electrical conductors are connected to each other and held at a first voltage. The charging and communication surface further comprises a plurality of second linear electrical conductors with exposed metal surfaces, the second linear electrical conductors being connected to each other and held at a second voltage different from the first. The first and second linear electrical conductors are disposed in alternating arrangement to form a flat surface, and adjacent conductors are spaced apart from each other. The charging and communication surface further comprises a controller including a modulator that imposes communications signals onto the voltage between the first and second linear conductors. In some embodiments, the charging and communication surface further comprises a demodulator that extracts communications signals from the voltage between the first and second linear conductors. In some embodiments, the charging and communication surface further comprises a power outlet configured to be connectable to another charging and communication surface in daisy chain fashion.

According to another aspect, a system for securely transporting medications or other items comprises a central computer system and a plurality relay trays. Each relay tray further comprises a lockable transportable container for holding items to be transported, an electronic controller including a processor and non-volatile memory, a power interface though which the relay tray can receive electric power, a communication interface through which the controller can communicate electronically, and a mechanism operable under control of the controller to make items in the locked container accessible in response to communications received via the communication interface, the mechanism operable by the controller only when power is being received through the power interface. The system further comprises a plurality of charging and communication stations in dispersed locations, each of the plurality of charging and communication stations including a power interface for supplying power to one of the relay trays at the station, and a first communication interface for communication with the relay tray at the station, and a second communication interface for communication with the central computer system. In some embodiments, the system further comprises an electronic network over which the central computer system communicates instructions to authorize access to the interiors of the lockable transportable containers. In some embodiments, the power interfaces of the relay trays and the charging and communication stations also serve as the communication interfaces of the relay trays and the first communications interfaces of the charging and communication stations. In some embodiments, each of the charging and communication stations comprises: a plurality of first linear electrical conductors with exposed metal surfaces, the first linear electrical conductors being connected to each other and held at a first voltage; and a plurality of second linear electrical conductors with exposed metal surfaces, the second linear electrical conductors being connected to each other and held at a second voltage different from the first; wherein the first and second linear electrical conductors are disposed in alternating arrangement to form a flat surface, and wherein adjacent conductors are spaced apart from each other. In some embodiments, the central computer system maintains an inventory of any medications stored in the plurality of relay trays. In some embodiments, the central computer system maintains an inventory of any controlled substances stored in the plurality of relay trays.

According to another aspect, a method of transporting an item comprises connecting, at a first workstation, a first source of power to a power interface of a relay tray. The relay tray comprises a lockable transportable container for holding items to be transported, an electronic controller including a processor and non-volatile memory, the power interface, a communication interface through which the controller can communicate electronically, and a mechanism operable under control of the controller to make items in the locked container accessible in response to communications received via the communication interface. The mechanism is operable by the controller only when power is being received through the power interface. The method further comprises placing the item to be transported into the relay tray, locking the relay tray, disconnecting the relay tray from the source of power, transporting the relay tray containing the item to a second workstation, and connecting, at the second workstation, a second source of power to the power interface of a relay tray. The method further comprises sending, at the second workstation, to the relay tray via the communication interface an instruction to make the item accessible. In some embodiments, connecting the relay tray to the first or second source of power comprises placing the relay tray on a charging and communication surface such that contacts on the relay tray come into contact with conductors in the charging and communication surface to supply power to the relay tray. In some embodiments, the method further comprises causing electronic communication to occur between the relay tray and the charging and communication surface via communications signals imposed onto the voltage between two of the conductors of the charging and communication surface, such that the power interface of the relay tray also functions as the communication interface of the relay tray.

DETAILED DESCRIPTION OF THE INVENTION

Figure 1:
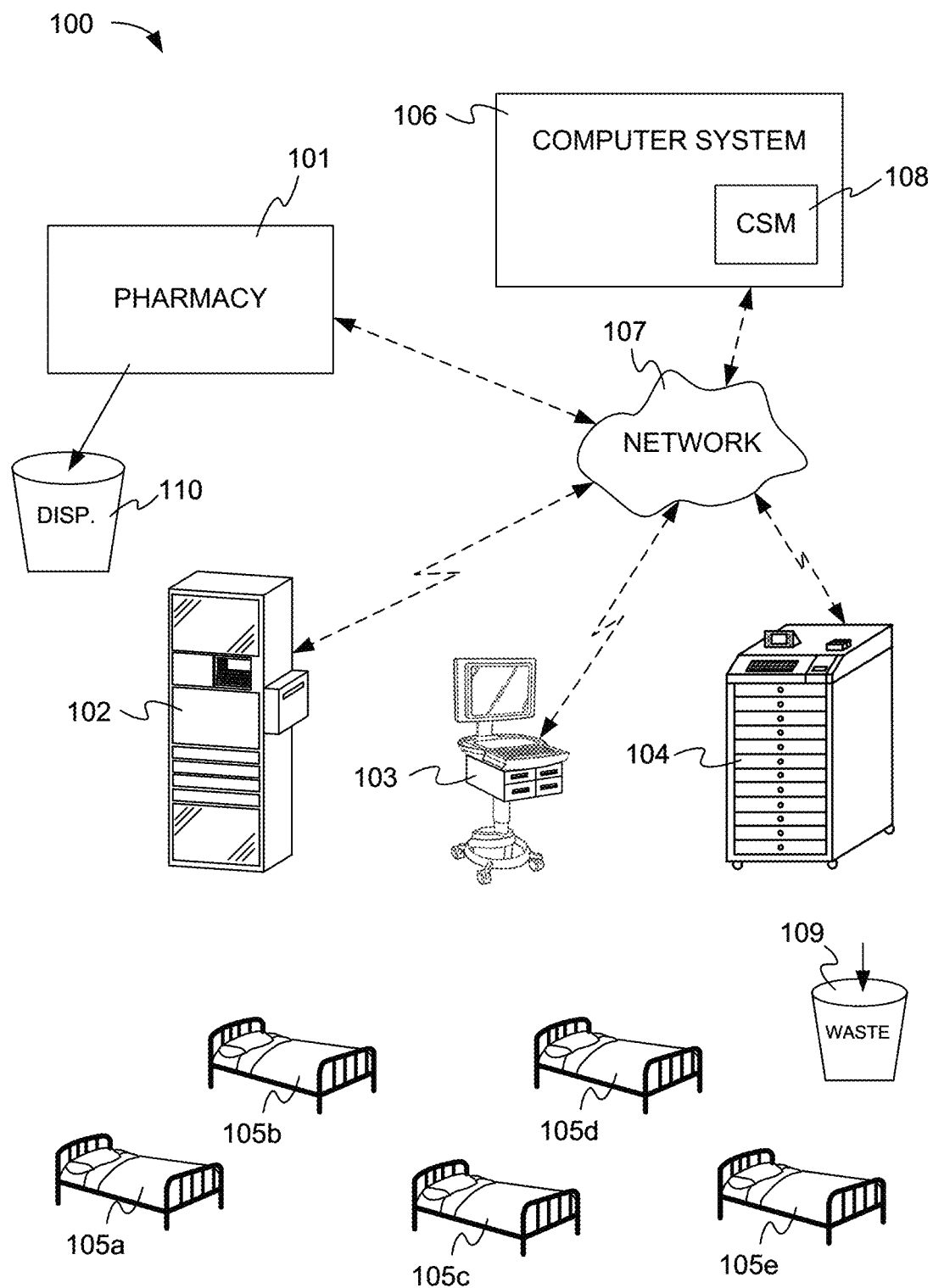
FIG. 1 illustrates an environment in which embodiments of the invention may find utility.

FIG. 1 illustrates an environment in which embodiments of the invention may find utility. Specifically, FIG. 1 illustrates a hospital environment 100, but it will be recognized that embodiments of the invention may be used in other environments as well.

In the example hospital environment of FIG. 1, a central pharmacy 101 serves as the primary medication storage location. However, various stationary cabinets 102, carts 103, portable cabinets 104, and other storage and dispensing devices may be stationed in different parts of the hospital, for temporary storage of medications and other items. For example, medications commonly used in a particular ward or department of the hospital may be stocked in a cabinet such as cabinet 102, for convenient access by floor personnel. In another example, medications expected to be dispensed to patients during a particular shift may be transferred to a dispensing cart 103 that can follow a nurse on his or her rounds to the patients in beds 105a-105e.

The various dispensing devices 102, 103, 104 may include devices such as those described in the following commonly owned U.S. Patents and patent applications, the entire contents of which are hereby incorporated by reference herein for all purposes: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on Aug. 19, 2003 to Lipps, U.S. Pat. No. 5,805,456, issued on Sep. 8, 1998 to Higham et al, U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Pat. No. 8,155,786 to Vahlberg et al., issued on Apr. 10, 2012, U.S. Pat. No. 8,073,563 to Vahlberg et al., issued on Dec. 6, 2011, U.S. Patent Application Publication No. 2008/0319577 of Vahlberg et al., published on Dec. 25, 2008, U.S. Pat. No. 8,140,186 to Vahlberg et al., issued on Mar. 20, 2012, U.S. Pat. No. 8,126,590 to Vahlberg et al., issued on Feb. 28, 2012, U.S. Pat. No. 8,027,749 to Vahlberg et al., issued on Sep. 27, 2011, U.S. Patent Application Publication No. 2008/0319790 of Vahlberg et al., published on Dec. 25, 2008, U.S. Patent Application Publication No. 2008/0319789 of Vahlberg et al., published on Dec. 25, 2008, U.S. Pat. No. 8,131,397 to Vahlberg et al., issued on Mar. 6, 2012, U.S. Patent Application Publication No. 2008/0319579 of Vahlberg et al., published on Dec. 25, 2008, U.S. Patent Application Publication No. 2010/0042437 of Levy et al., published on Feb. 18, 2010, and U.S. Patent Application Publication No. 2016/0253860 of Wilson et al., published on Sep. 1, 2016. Embodiments of the present invention may incorporate features from the devices described in these documents, in any workable combination.

A computer system 106 may execute a program for tracking of medications and supplies throughout the hospital, and may communicate via electronic network 107 with the various dispensing devices 102, 103, 104, to record transactions involving medications or supplies. Electronic network 107 may be a wired network, a wireless network, or may have both wired and wireless portions. Any suitable networking technology or combination of technologies may be used, for example WiFi™, Bluetooth™, Ethernet, a cellular data network, or other technologies.

Computer system 106 may be informed when a particular medication is removed from or returned to one of the dispensing devices. In particular, computer system 106 may execute a controlled substance management (CSM) application 108, for particular tracking of legally controlled substances. Additional details of systems and methods for tracking supplies, including controlled substances, may be found in U.S. Patent Application Publication Number 2013/0006652 of Vahlberg et al., published on Jan. 3, 2013, the entire contents of which are hereby incorporated by reference herein for all purposes.

Ideally, medications leave the system in only three ways. In a first way, medication is administered to a patient. In a second way of leaving the system, medication may be wasted. For example, if the medication is packaged in a quantity that exceeds the prescribed dose for a particular patient, each administration may result in a leftover amount that is not reusable, and must be discarded 109. In another example of waste, a vial may be dropped and broken, rendering its contents unusable. In a third way of leaving the system, medication may be returned to pharmacy 101 for disposal in a controlled manner 110, for example because the medication has reached its beyond use date.

However, medications can also leave the system in other ways, for example due to inadvertent mistake, but also intentionally for illicit use or sale. The illicit removal of controlled substances is known in the art as diversion. It is highly desirable to prevent or at least discourage diversion of medications and supplies.

Computer system 106 may track the movements of medications and supplies into and out of pharmacy 101 and dispensing devices 102, 103, 104. However, many transfers of items are required. For example, a pharmacy technician may periodically physically visit dispensing devices 102, 103, 104 to restock depleted items, and to recover returned or unused items. This requires transferring of items from pharmacy 101 to the technician's cart, and transferring the items again from the technician's cart to the dispensing devices. Later, a nurse will remove the items from the dispensing devices. Each of these transfers must be tracked and documented. In addition, substantial pharmacy time is consumed in making the rounds to the dispensing devices. Similar transfers and documentation are required for moving items from the dispensing devices back to the pharmacy.

Relay boxes have been developed for transferring items via normal intra-facility mail systems and the like. A relay box is a secure transportable container that can preferably be conveniently opened only at the location where it is filled (for example pharmacy 101) or at its destination (for example a nurse station). Medications or supplies may then be transferred from the relay box to a dispensing device, or may be used immediately. More detail about relay boxes may be found in U.S. Patent Application Publication No. 2017/0228951 of Foot et al., published Aug. 10, 2017, the entire disclosure of which is hereby incorporated by reference herein for all purposes.

According to embodiments of the invention, items are packaged in relay trays that have expanded features as compared with relay boxes.

Figure 2:
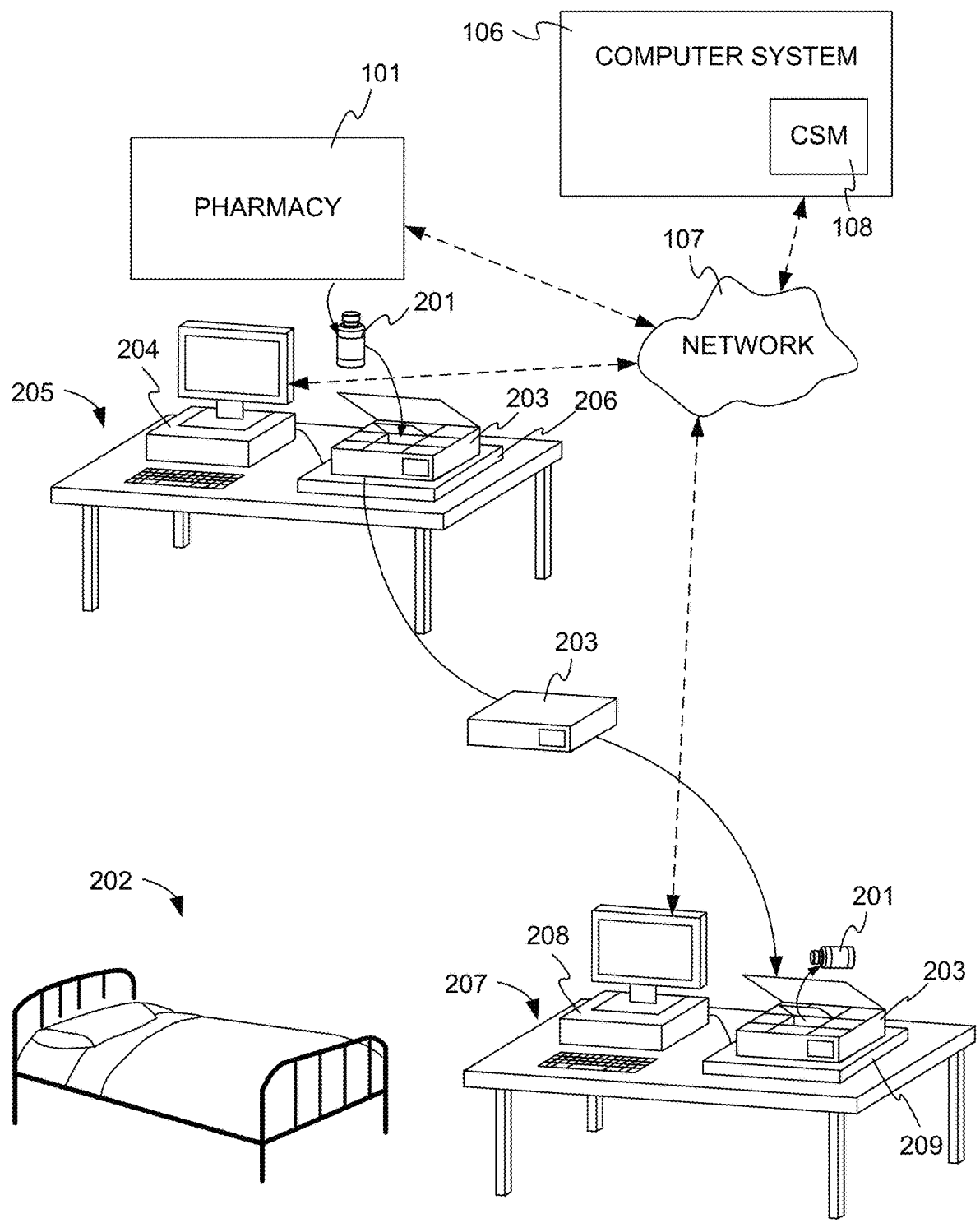
FIG. 2 illustrates the use of a relay tray in a hospital environment, in accordance with embodiments of the invention.

FIG. 2 illustrates the use of a relay tray in a hospital environment. In the example depicted, it is desired to transport a vial 201 of medication from pharmacy 101 to a patient room 202. A relay tray 203 is used to transport vial 201. Relay tray 203 is a transportable secure container with an electronically-controlled locking mechanism. Like a relay box, a relay tray in accordance with embodiments of the invention is a secure container that can preferably be conveniently opened only at the location where it is filled or at its destination. Vial 201 is placed in relay tray 203, and relay tray 203 is locked under control of a computer 204 at a workstation 205. Computer 204 is in communication with computer system 106, which oversees the process and records the transfer of vial 201 into relay tray 203. Relay tray 203 is locked in response to a command from computer 204, in accordance with instructions from computer system 106.

Relay tray 203 includes an electronic controller that is powered while relay tray is at workstation 205. For example, relay tray 203 may receive power and communication through a docking and communication surface 206, or directly through a cable (not shown). Information about the contents of relay tray 203 may be written to nonvolatile memory within the controller. For example, a listing of items within relay tray 203 may be written to the memory. Other information may be written to the nonvolatile memory as well, for example an indication of the room number or other destination of the relay tray, an identifier of the patient for whom the contents of the relay tray are intended, or other information. The controller may conveniently be in a "false bottom" of relay tray 203, or any other workable position.

In some embodiments, each relay tray 203 is assigned a unique serial number or other identifier, which is stored within relay tray 203. For example, the unique identifier may be stored in the nonvolatile memory, in a secure element, in an identifying tag as described below, or in another location or in a combination of locations. The unique identifier is preferably difficult or impossible to change, so that each relay tray 203 is permanently uniquely identified.

Once relay tray 203 is locked and removed from workstation 205, it may be completely unpowered, and may not include a battery or other power source. In other embodiments, relay tray 203 may include a small battery or capacitor for maintaining timekeeping circuitry, tracking, and the like, but even in this case, relay tray 203 preferably has no means for unlocking itself when it is disconnected from an external power source as may be found at a workstation such as workstation 205. This inability to unlock when not at a suitable workstation makes transport of items in relay tray 203 secure. Without a suitable electronic connection and command from computer system 106, items in relay tray 203 cannot be removed without physically damaging relay tray 203. In some embodiments, a mechanical means may be provided for opening a locked relay tray, for example a key that can be used in the event of a power failure or other emergency. Preferably, the access to the key is tightly controlled and permitted only to authorized personnel.

As is shown in FIG. 2, relay tray 203 (with vial 201 inside) is transported to another workstation 207 in or near patient room 202. Relay tray 203 is placed in connection with computer 208, for example using another docking and communication surface 209. In accordance with instructions from computer system 106, relay tray 203 is opened, and vial 201 can be removed so that the medication in vial 201 can be administered to the patient. Preferably, relay tray 203 authenticates computer system 106 before opening, to ensure that the instruction to open came from a legitimate source.

Any patient information stored in relay tray 203 may be hashed, so that it is unique to the intended patient, but not human-readable. For example, the patient's name may be hashed using an agreed-upon algorithm at workstation 205, and the result stored in the nonvolatile memory within relay tray 203. When relay tray 203 arrives at workstation 207, the name of the patient in room 202 may be hashed using the same algorithm, and the result compared with the hashed name stored in relay tray 203, to help verify that relay tray 203 has reached the correct patient. In this way, the patient's name is not displayed or otherwise available while relay tray 203 is in transit, in the interest of patient privacy. In other embodiments, patient information stored in relay tray 203 may be encrypted, and recoverable only at an authorized and authenticated location such as workstation 207.

Preferably, relay tray 203 will not unlock at workstation 207 until it is confirmed that relay tray 203 has arrived at its correct destination for the correct patient. The confirmation is preferably performed over the authenticated channel between relay tray 203 and computer system 106.

While FIG. 2 shows transporting relay tray 203 within a facility, relay trays may be transported between facilities, which may be widely separated. For example, a relay tray 203 may be shipped to nearly any location, for example to restock medication supplies at a nursing home or to deliver medications to a patient in home care. The shipment may be by any suitable means, including ground or air shipment. A relay tray lacking a battery may be especially amenable to air shipment.

Figure 3:
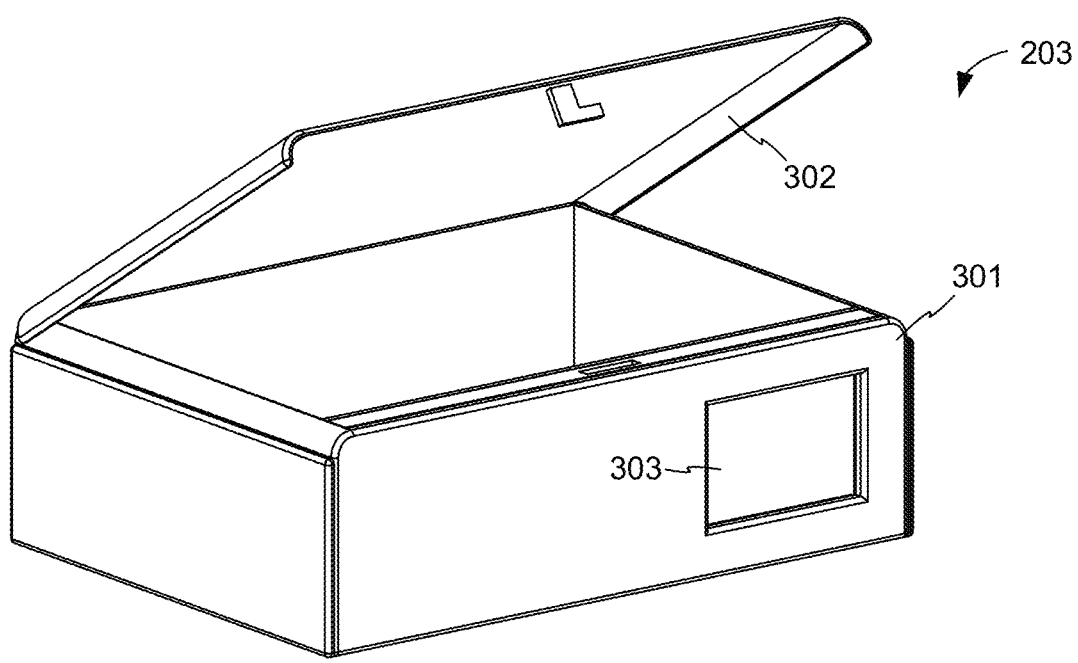
FIG. 3 shows the relay tray of FIG. 2 in more detail, in accordance with embodiments of the invention.

FIG. 3 shows relay tray 203 in more detail, in accordance with embodiments of the invention. Relay tray 203 includes a main container portion 301 defining a compartment of the relay tray, and a hinged lid 302. In other embodiments, a sliding, removable, or rotating lid may be used, or another suitable kind of lid. A relay tray in accordance with embodiments of the invention may be of any suitable size. For example, relay tray 203 may conveniently be about 10 to 14 inches wide, about 8 to 12 inches deep, and about 3 to 5 inches high. Other larger or smaller sizes are possible. In many embodiments, a relay tray is of a suitable size to be transported throughout a facility in a manner similar to internal mail. However, in some embodiments, a relay tray embodying the invention may be too large or heavy to be carried by an unassisted person.

The outer shell of relay tray 203 may preferably be made of a strong, durable material such as steel, aluminum, a reinforced polymer, or another suitable material, or a combination of materials. In some embodiments, lid 302 may be transparent or translucent, or include a transparent portion so that the contents of relay tray 203 may be visible when lid 302 is closed. Relay tray 203 is preferably readily cleanable.

Relay tray 203 further includes a display 303, which may display a destination address for relay tray 203, an identifier of a patient for which the contents of relay tray 203 are intended, or other information. Display 303 may be simply a typed or written label attached to any part of relay tray 203, or may be an electronic display. Preferably, any electronic display is nonvolatile, so that information on display 303 can be read during transport, in the absence of any power input into relay tray 203. For example, display 303 may be an electrophoretic or other "electronic paper" display than remains readable even when unpowered. Such displays are manufactured by E-Ink Corporation of Billerica, Mass., USA and others.

In some cases, multiple different medications intended for different patients may be transported in relay tray 203. For example, medications may be transported to the same nursing station near which two patients are located. In that case, both patient names or other identifiers may be hashed and stored in relay tray 203. To implement usage of a single relay tray for the benefit of multiple patients, a relay tray may be logically defined as multiple trays.

Figure 4:
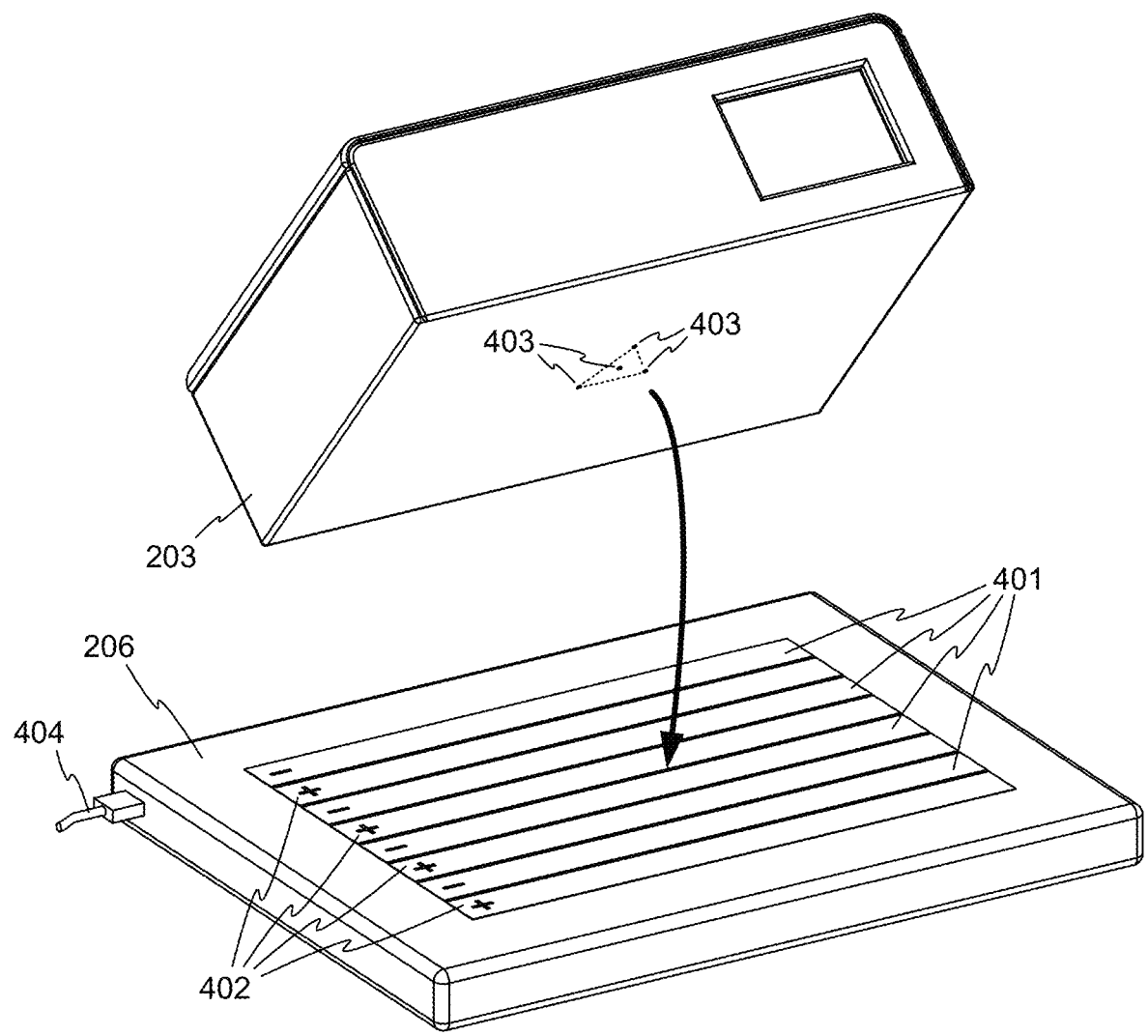
FIG. 4 illustrates the relay tray of FIG. 2 and a docking and communication surface, in accordance with embodiments of the invention.

FIG. 4 illustrates relay tray 203 and docking and communication surface 206, in accordance with embodiments of the invention. Docking and communication surface 206 includes a set of exposed metal conductors 401 and 402, alternating ones of which are held at different voltages. In the example of FIG. 4, conductors 401 are held at a low or ground voltage, and conductors 402 are held at a higher voltage, for example 12V DC or another suitable voltage. Gaps are provided between the alternating conductors 401 and 402, such that adjacent conductors 401 and 402 are spaced apart from each other.

Relay tray 203 includes a set of four contacts 403, exposed on an outside surface of relay tray 203. In this example, contacts 403 are on the bottom surface of relay tray 203. Contacts 403 are smaller in diameter than the spacing between conductors 401 and 402, so none of contacts 403 can touch adjacent conductors 401 and 402 at the same time. However, when relay tray 203 is placed with its bottom surface down on docking and communication surface 206, at least one of contacts 403 will touch one of lower-voltage conductors 401, and at least one of contacts 403 will touch one of higher-voltage conductors 402. Rectifier circuitry within relay tray 203 generates DC voltage of a polarity suitable for powering electronics within relay tray 203 when any one of contacts 403 is held at the lower voltage and any one of the other three contacts 403 is connected to the higher voltage, regardless of whether each of the remaining two of the electrical contacts is held at the lower or higher voltage. In some embodiments, contacts 403 and docking and communication surface 206 may conform to the Open Dots™ standard, which specifies a workable set of dimensions for conductors 401 and 402, and contacts 403. In an embodiment according to the Open Dots™ standard, contacts 403 would have a maximum diameter of 1.8 mm, and would be placed at the center and vertices of an equilateral triangle, such that the outer three contacts are on a circle having a nominal radius of 9.73 mm. Each of conductors 401 and 402 would be between 10.09 and 10.18 mm wide, conductors 401 and 402 would be nominally spaced at 12.2 mm intervals, and adjacent conductors 401 and 402 would be separated by nonconductive areas between 1.86 and 1.96 mm wide. Other arrangements are possible.

In other embodiments, relay tray 203 may receive power and communication signals through a cable, rather than through contacts such as contacts 403. In other embodiments, relay tray 203 may receive power and communication signals through inductive coupling. For example relay tray 203 may include a wire coil near its bottom surface or at another location. The wire coil may be used to receive power and exchange communication signals with another wire coil at a workstation. An inductive interface may include features similar to those of an interface according to the Qi interface standard promulgated by the Wireless Power Consortium. Multiple power and communication interfaces may be provided. For example, any or all of a cable connection, an inductive connection, and contacts such as contacts 403 may be provided, so that relay tray 203 can be used at workstations having different capabilities.

Docking and communication surface 206 can communicate with a computer such as computer 204 via cable 404, or may communicate wirelessly. Docking and communication surface 206 may receive power through cable 404, or through a dedicated power connection (not shown).

Figure 5:
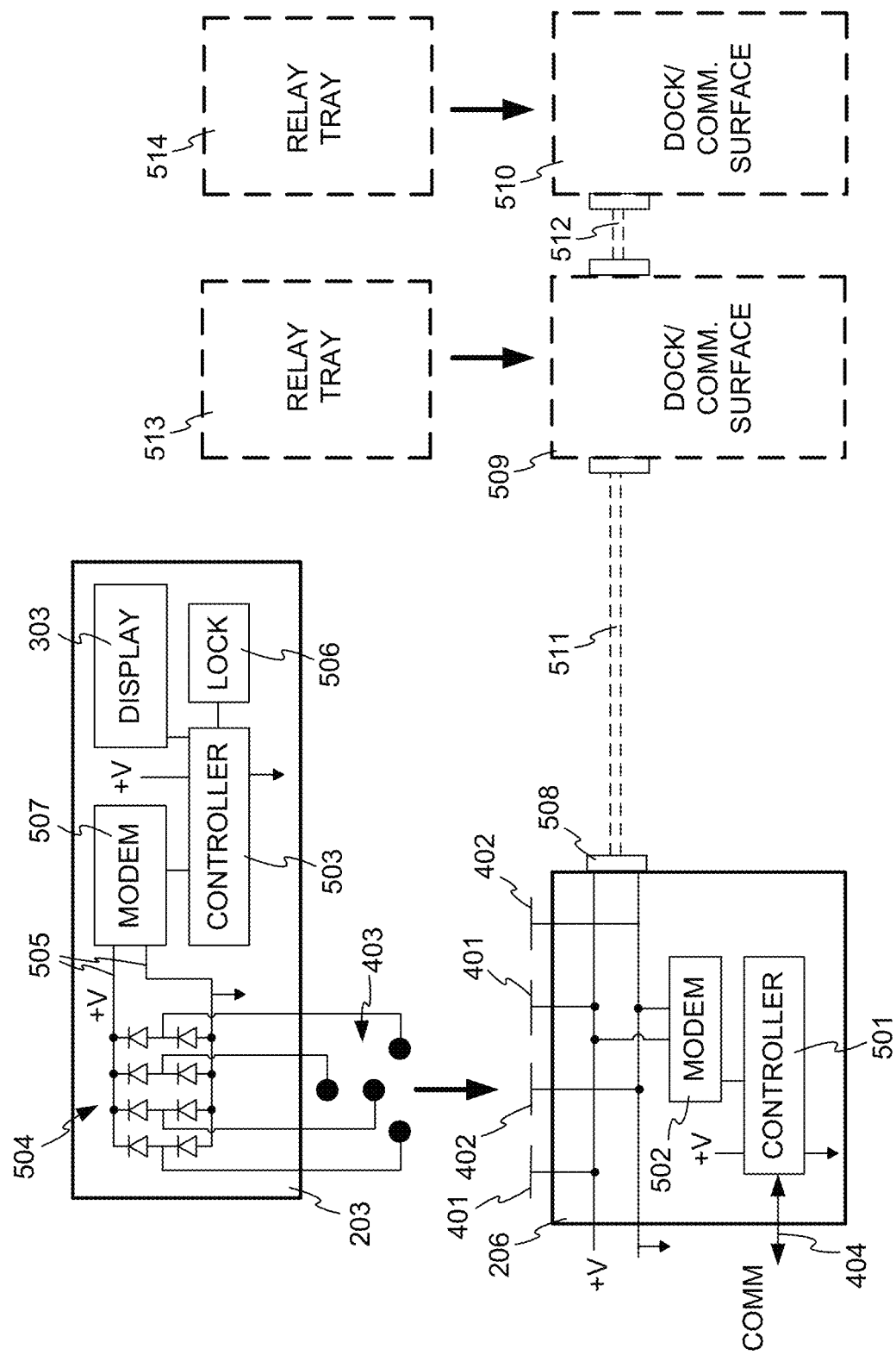
FIG. 5 illustrates simplified electrical block diagrams of the relay tray and the docking and communication surface of FIG. 4.

FIG. 5 illustrates simplified electrical block diagrams of docking and communication surface 206 and relay tray 203, juxtaposed with contacts 403 of relay tray 203 about to contact conductors 401 and 402 of docking and communication surface 206. Docking and communication surface 206 includes a controller 501, which may in turn include a processor, memory, and other circuitry for performing the functions of docking and communication surface 206. Docking and communication surface 206 receives power from an external source, for example mains power, a power supply, or a cable from an attached computer. Docking and communication surface 206 passes voltages to conductors 401 and 402 on the surface of docking and communication surface 206. While FIG. 5 shows the voltages received by docking and communication surface 206 being simply passed through to conductors 401 and 402, other arrangements are possible. For example, docking and communication surface 206 may receive power from the mains and may rectify and filter the power to provide DC voltages to conductors 401 and 402. Docking and communication surface 206 is also in electronic communication with an attached computer, for example via cable 404 or another communication mechanism. In some embodiments, the power and communication connections to docking and communication surface 206 are carried by a single multi-conductor cable, for example a Universal Serial Bus (USB) cable or another kind of cable.

Docking and communication surface 206 further includes a modulator and a demodulator, represented as modem 502.

Relay tray 203 also includes a controller 503, which may include another processor, memory, and other circuitry for carrying out the functions of relay tray 203. Relay tray 203 includes a rectifier 504, which produces voltage at terminals 505 of the correct polarity to operate controller 503, regardless of which of contacts 403 are against which of conductors 401 and 402. The received voltage is used to power controller 503 and other functions of relay tray 203. Controller 503 controls an electromechanical lock 506, and can cause information to be displayed on display 303.

Relay tray 203 also includes a modulator and demodulator, shown as modem 507. Docking and communication surface 206 and relay tray 203 can communicate through conductors 401 and 402 and contacts 403 by imposing (modulating) communication signals onto the DC power lines by the transmitting device and by extracting (demodulating) the signals by the receiving device. For example, the imposed signals may be of a relatively high frequency that is detectable by the respective demodulators, but has little or no effect on the quality of the power carried by the same lines.

Docking and communication surface 206 may include a power outlet connection 508, allowing additional docking and communication surfaces such as surfaces 509 and 510 to be daisy chained together, each receiving power from the last, for example via cables 511 and 512. Additional relay trays such as trays 513 and 514 may be placed on surfaces 509 and 510. Once placed, the additional relay trays are powered up and can communicate with docking and communication surface 206, and ultimately computer system 106, via the power connections between the docking and communication surfaces.

Figure 6:
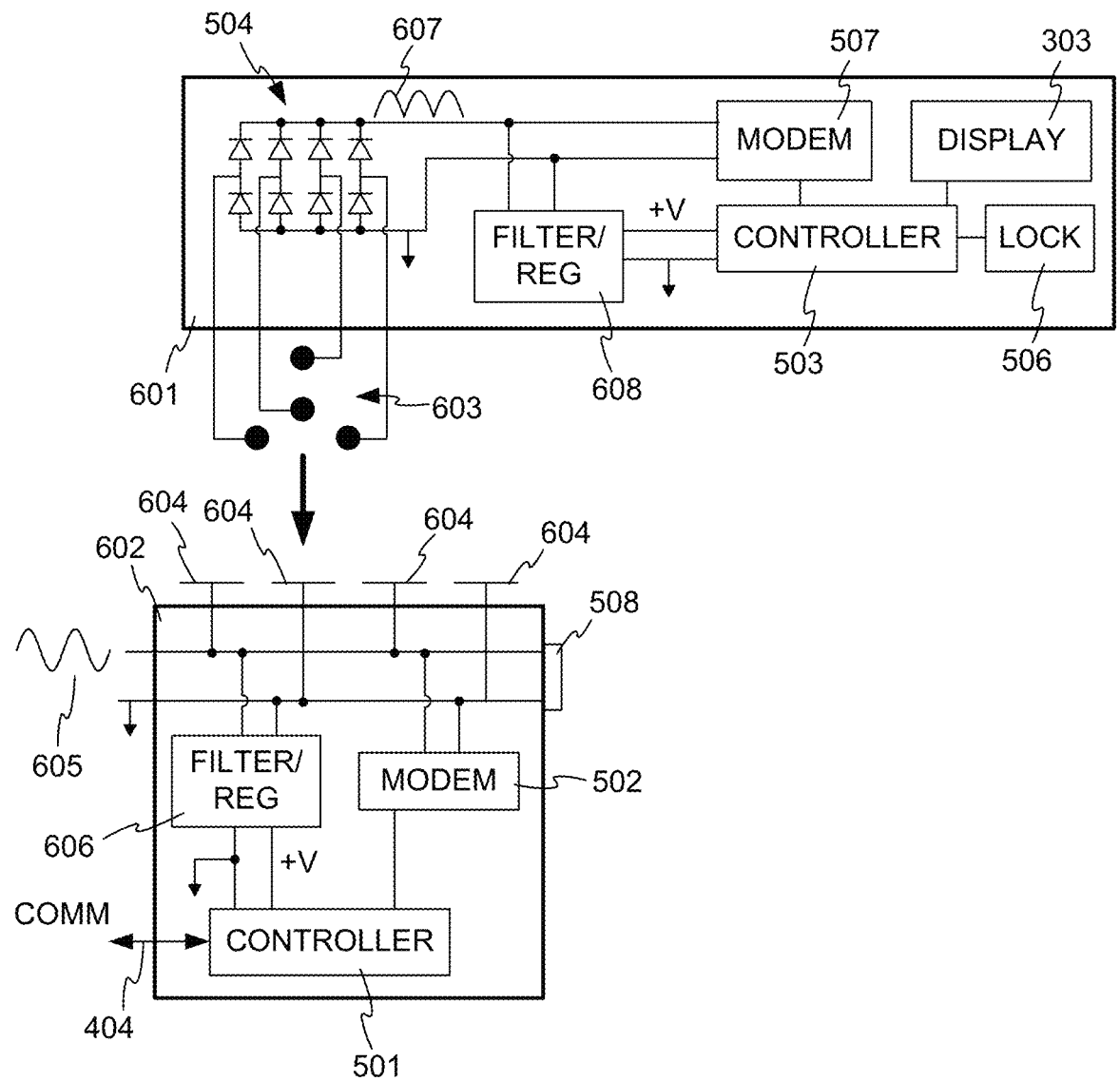
FIG. 6 illustrates simplified electrical block diagrams of a relay tray and a docking and communication surface in accordance with another embodiment.

In the embodiment of FIGS. 4 and 5, the power interface between relay tray 203 and docking and communication surface 206 uses direct current (DC). In other embodiments, alternating current (AC) may be used. FIG. 6 illustrates electrical block diagrams of a relay tray 601 and a docking and communication surface 602 in accordance with an AC embodiment. Relay tray 601 may include contacts 603 on an outer surface, similar to contacts 403 of relay tray 203 described above. Docking and communication surface 602.

Docking and communication surface 602 includes exposed conductors 604 in an outside surface, similar to conductors 401 and 402 of docking and communication surface 206 described above. Docking and communication surface 602 receives AC power 605, and passes it to conductors 604, for transfer to relay tray 601 through contacts 603. Docking and communication surface 602 conditions the AC power, for example using a filter and regulator 606, to provide DC power for powering controller 501. Controller 501 is in communication via a cable 404 with an external computer system, and controls modem 502 to impose and extract communications signals onto and from the AC signal. The AC signal may be provided to a power outlet connection 508, to allow multiple relay trays to be connected together in daisy chain fashion.

Relay tray 601 includes a rectifier 504 which, when supplied with AC power 605, produces rectified AC power 607. A filter and regulator 608 provides DC power to controller 503, which controls lock 506, modem 507, and display 303.

In the example of FIG. 6, docking and communication surface 602 receives low voltage AC power 605 at, for example 12 volts or another suitable voltage. Thus, the voltage on exposed conductors 604 is also low voltage and safe for operators. In other embodiments, AC power 605 may be received at line voltage, for example 110 volts. In that case, docking and communication surface 602 may include a transformer or other circuitry for stepping down the line voltage to a lower voltage before providing it to conductors 604.

In any event, the voltage at conductors 604 is highly preferably not line voltage, but is a safe low voltage, for example less than about 50 volts.

Whether the voltage produced at the conductors of a docking and communications surface is AC or DC, short circuit protection is preferably provided, for example as specified in the Open Dots™ standard, or in another arrangement.

In some embodiments, the communications carried out over the power line connection between docking and communication surface 206 and relay tray 203 may conform to or resemble communications described in the G3-PLC power line communication standard promulgated by the G3-PLC Alliance. Such communications use orthogonal frequency division multiplexing sampled at 400 kHz, with adaptive modulation and tone mapping. Error detection and correction may be made by a convolutional code and Reed-Solomon error correction.

In other embodiments, the communications between docking and communication surface 206 and relay tray may conform to or resemble communications described in the PRIME power line communication standard promulgated by the PRIME Alliance. Any other suitable standard or propriety communication format may be used as well, for example IEEE 1901.2. In other embodiments, broadband power line communication may be used, for example similar to the arrangement used in the HomePlug® standard promulgated by the HomePlug Powerline Alliance.

As is discussed above, relay tray 203 preferably authenticates computer system 106 before opening, to ensure that the instructions to open originated from an authorized source. In this way, illicit "open" instructions can be detected and ignored. The authentication can be performed in any suitable way, but in some embodiments, may be performed using public key authentication.

In public key authentication, computer system 106 has public and private keys, and creates a signature using both. Relay tray 203 knows the public key of computer system 106, and can determine using it whether the signature is genuine, although relay tray 203 need not and does not have the private key of computer system 106.

Figure 7:
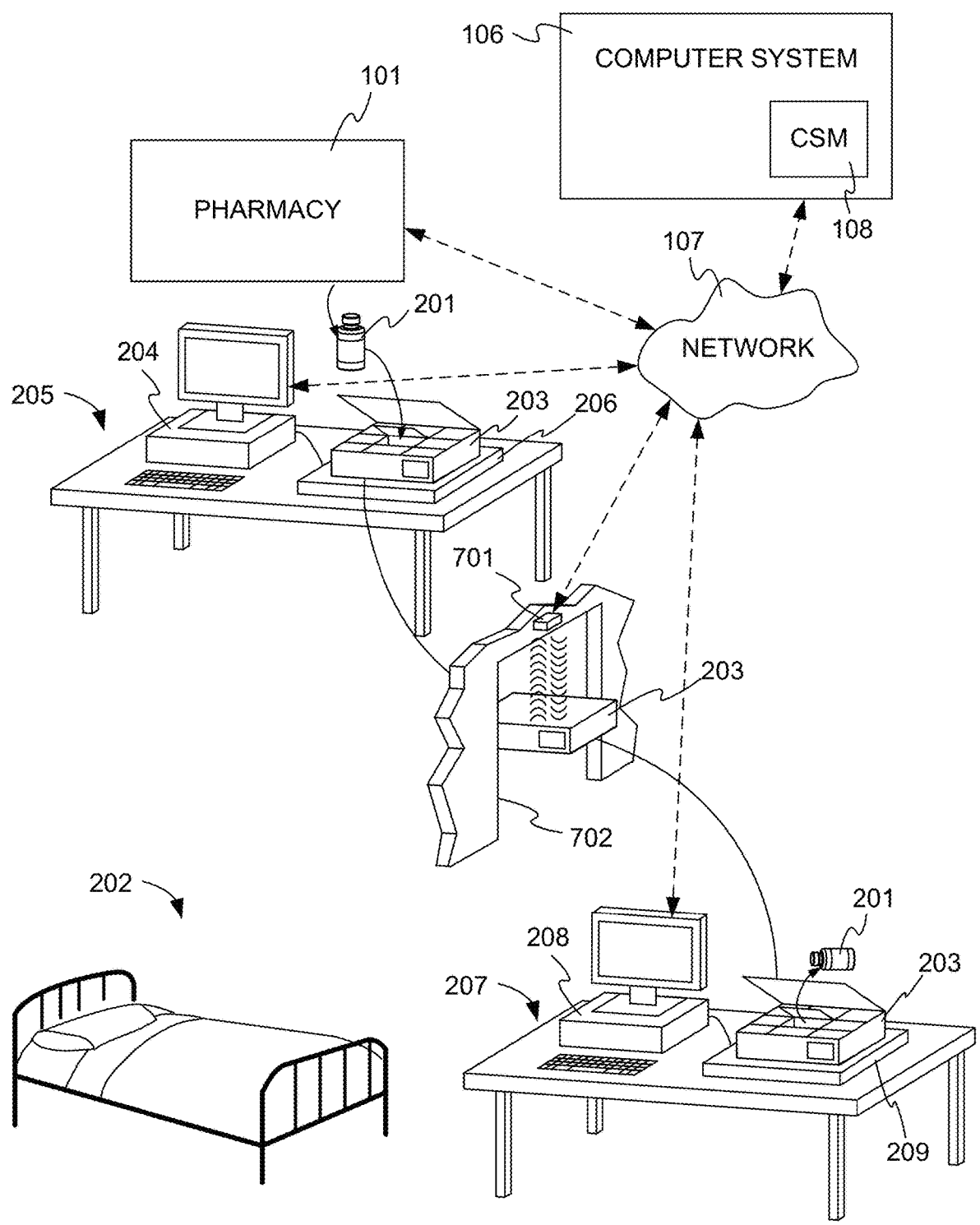
FIG. 7 illustrates a wireless reading station installed in doorway, in accordance with embodiments of the invention.

In some embodiments, a relay tray such as relay tray 203 may include a passive, externally-excitable memory device such as a radio frequency identification (RFID) tag or similar device. An identifier of relay tray 203 may be stored in the RFID tag, and used for additional tracking of relay tray 203 within a facility. For example, as is shown in FIG. 7, a wireless reading station 701 is installed in doorway 702, through which relay tray 203 may pass on its way from workstation 205 to workstation 207. Wireless reading station 701 may excite an RFID tag or other device within relay tray 203, causing relay tray to divulge its stored identifier. Reading station 701 can receive the identifier and send it to computer system 106, which can record the fact that relay tray 203 passed through doorway 702. Other information such as the time and date of the passage may be recorded. Reading stations 701 may be placed at multiple locations around the facility, so that relay trays can be passively tracked if desired. Reading stations may be placed at the exits of the facility, so that any attempt to remove a relay tray from the premises will be detected. In some instances, such removal may be legitimate, for example when a medication or other item is being shipped to another location in a relay tray. In other cases, removal of a relay tray from the facility may signal a diversion attempt.

Tracking of relay trays throughout a facility may be accomplished in other ways as well. For example, a relay tray that includes a battery may also include a low power wireless receiver such as a Bluetooth® LE or another similar receiver. (As is discussed above, the battery preferably does not supply power to any mechanism for unlocking the relay tray or otherwise retrieving items from the relay tray during transit.) A number of beacon transmitters may be placed in known locations around the facility. During transport, the relay tray may periodically or occasionally, for example every few seconds, detect any nearby beacons, and record the time that any beacon is detected. Once the tray arrives at its destination and is connected to a communication interface, the record of detections can be retrieved. The journey of the relay tray from one workstation to the other can be reconstructed based on the known locations of the beacon transmitters. Any deviations from an expected route or timing of the journey may signal attempted diversion. The records of the journeys of the relay trays may be used for analytic purposes as well, for example to optimize pharmacy cart routes for fastest or most efficient delivery, or the like.

Beacon-based tracking may be implemented even for relay trays that have no batteries, for example by transporting the relay trays on carts that have power-only docking surfaces or other suitable power connections. A power-only docking surface may outwardly be similar to docking and communication surface 206 or 602 described above, but lacks any capability to communicate through the power interface, for example through conductors such as conductors 401 and 402 or via an inductive coil. Thus, a relay tray positioned on a power-only docking surface may be able to operate a beacon receiver using power received through its surface contacts or coil, but will not unlock itself or otherwise make its contents accessible because it cannot receive any instruction to do so from computer system 106. In other embodiments, a simple plug-in power-only connection may be provided between a transport cart and a relay tray, so that the relay tray can receive power to perform tracking, but will not open during transport.

While relay tray 203 has only one compartment, other relay trays may be more complex. For example, a relay tray embodying the invention may have multiple compartments, which may be individually lockable.

Figure 8:
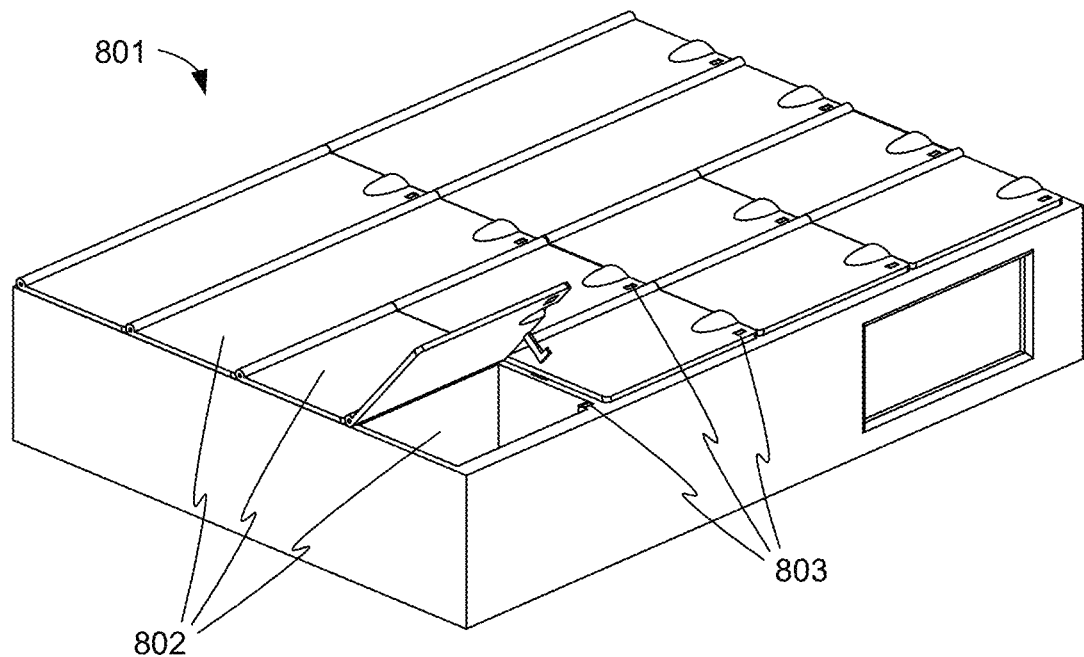
FIG. 8 illustrates a relay tray in accordance with other embodiments.

FIG. 8 illustrates a relay tray 801 in accordance with other embodiments. Relay tray 801 includes several individually-lockable compartments 802. Guiding lights 803 may be provided, so that a user retrieving medication from relay tray 801 for a particular patient can be guided to the correct compartment 802. For example, at the time relay tray 801 is loaded at workstation 205, computer system 106 can record which medications are placed in which compartments 802 of relay tray 801. Once relay tray 801 arrives at patient room 202 and a medication is to be retrieved for administration to a patient, computer system 106 can instruct relay tray 801 to illuminate the guiding light 803 corresponding to the compartment 802 holding the medication for the patient. Relay tray 801 can illuminate the correct guiding light 803 and unlock the correct compartment 802.

A relay tray such as relay tray 801 with multiple compartments may be especially useful for transporting medications for more than one patient, for transporting multiple medications for a single patient, or for transporting multiple doses of a controlled substance. For example, medication may be loaded into relay tray 801 with a single dose per small compartment. The compartments can be opened only upon instructions from computer system 106, which may issue the instructions one at a time according to the dosage schedule of the particular medication. Thus, only one dose of the medication can be accessed at a time, reducing opportunities for dosing errors or diversion.

In some embodiments, a relay tray such as relay tray 801 may store a record of which medications are stored in which compartments 802. For example, the record may be stored in nonvolatile memory within relay tray 801 when relay tray 801 is loaded at pharmacy 101. In this arrangement, computer system 106 does not need to track medications to the compartment level, but only needs to track which medications are in which relay tray. To dispense an item, computer system 106 may simply send an instruction to relay tray 801 to dispense one dose of a particular medication. Relay tray 801 can confirm that the medication is present, locate the correct compartment 802 using its internal record, illuminate the correct guiding light 803, and open the compartment 802. The interface between computer system 106 and relay tray 801 in this arrangement may be called a medication abstraction layer, because instructions from computer system 106 need only reference medications, and not specific compartments 802.

In other embodiments, computer system 106 may track items to the compartment level. In this arrangement, computer system 106 stores a record of which medications are in which compartments of which relay trays. The record is constructed when the relay tray is loaded at pharmacy 101. To dispense an item, computer system 106 sends an instruction to relay tray 801 to unlock a specific compartment 802. In this arrangement, no abstraction is involved, and relay tray 801 may or may not have a record of the contents of compartments 802.

Figure 9:
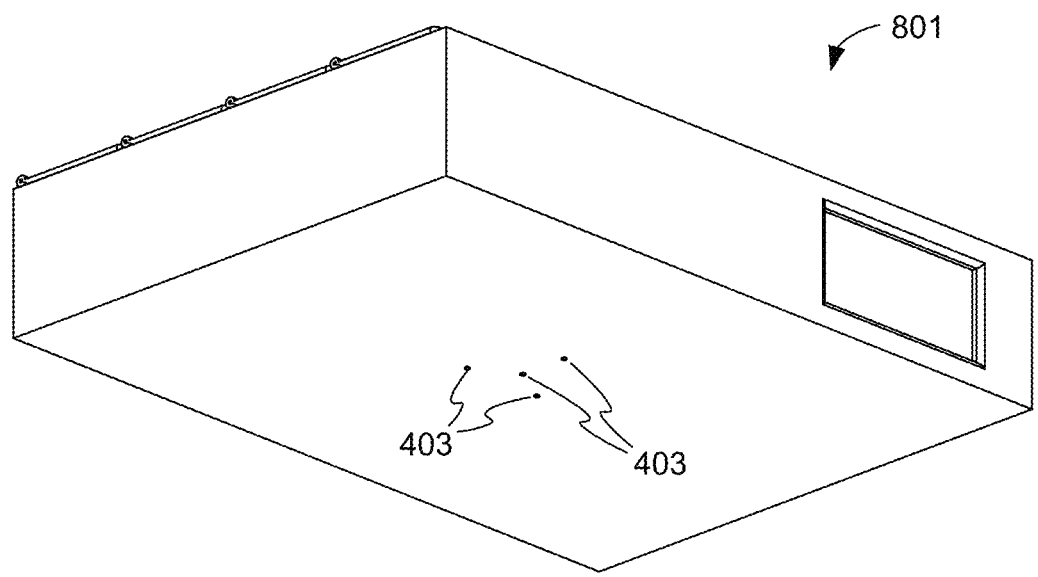
FIG. 9 shows a lower oblique view of the relay tray of FIG. 8.

FIG. 9 shows a lower oblique view of relay tray 801. In this example, relay tray 801 has contacts 403 on its bottom side, like contacts 403 of relay tray 203 described above. Relay tray 801 can thus receive power and communication signals from a docking and communication surface such as docking and communication surfaces 206 and 209. In other embodiments, relay tray 801 may be connected to a computer at a workstation using a cable carrying power and communications signals, instead of using a docking and communication surface. In that case, relay tray 801 may not include contacts 403. In other embodiments, both a cable connection and contacts such as contacts 403 may be provided, so that relay tray 801 can be used at workstations having different capabilities.

Figure 10:
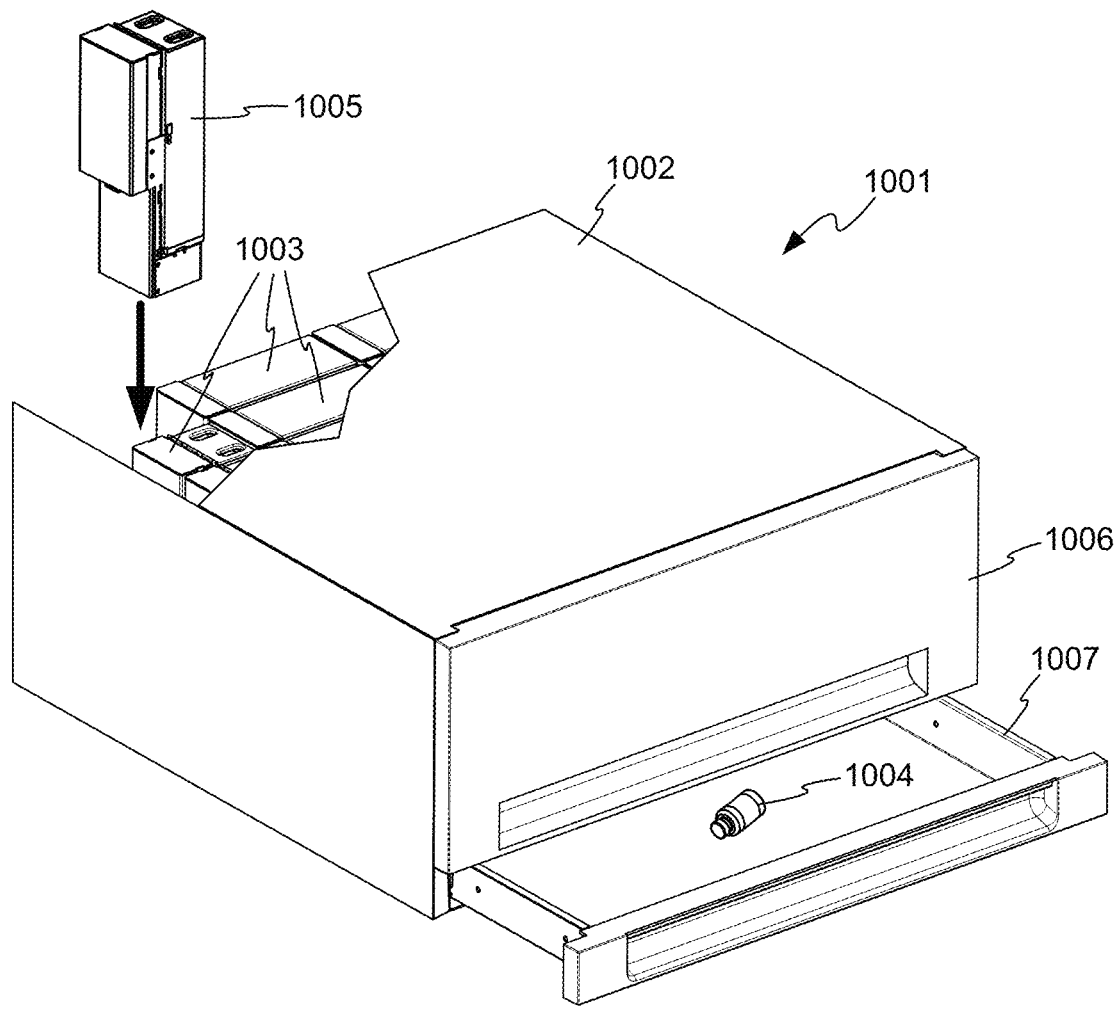
FIG. 10 illustrates a relay tray in accordance with other embodiments.

FIG. 10 illustrates a relay tray 1001 in accordance with other embodiments. Relay tray 1001 has features that may be especially useful in the transport of controlled substances, although it may be used for transport and dispensing of any compatible kind of item. Relay tray 1001 includes a cabinet 1002 housing a number of dispensing mechanisms 1003. Dispensing mechanisms 1003 are electromechanical devices that can dispense a single dose at a time of a medication. Each dispensing mechanism 1003 holds a supply of the items to be dispensed, and can dispense them one at a time under control of a controller within relay tray 1001. Different dispensing mechanisms may be configured to dispense oral solids in blister packs, syringes, vials such as vial 1004, or other kinds of items. Relay tray 1001 may be configured with different mixes of types of dispensing mechanisms 1003, depending on the expected usage of medication package types. One dispensing mechanism 1005 is shown being inserted into relay tray 1001. Preferably, each dispensing mechanism 1003 makes electrical and mechanical connection with structure (not shown) inside of relay tray 1001 upon insertion. In other embodiments, a relay tray may include only a single dispensing mechanism, for example a mechanism integrated into the structure of the relay tray.

In use, dispensing mechanisms 1003 are preferably loaded at pharmacy 101 with medications or other items to be dispensed, and are locked inside of relay tray 1001. For example, dispense drawer 1006 may be opened, giving pharmacy personnel access to dispensing mechanisms 1003. Once dispensing mechanisms 1003 are loaded, dispense drawer 1006 can be closed and locked.

During transport, relay tray 1001 is unpowered, and the dispensing mechanisms cannot be used to dispense items. When relay tray 1001 is connected to power and a network at a workstation such as workstation 207, relay tray 1001 can dispense individual items in response to commands from computer system 106. Relay tray 1001 may include contacts such as contacts 403 to receive power and communication signals from a docking and communication surface, or relay tray 1001 may receive power and communication signals through one or more cables. In other embodiments, both a cable connection and contacts such as contacts 403 may be provided.

Each dispensing mechanism 1003 may drop items downward into dispense drawer 1007, which can be pulled out of relay tray 1001 to reveal the dispensed item. The user of relay tray 1001 thus does not have access to the interior of relay tray 1001 or dispensing mechanisms 1003. This arrangement reduces opportunities for human error and restricts access to the medications inside of relay tray 1001, possibly deterring diversion. Examples of dispensing devices suitable for use in embodiments of the invention are described in U.S. Patent Application Publication No. 2016/0253860 of Wilson et al., previously incorporated by reference. Other kinds of dispensing devices may also be used in other embodiments of the invention.

A system of relay trays and workstations may be used as part of a medication distribution and management system within a hospital or other facility. For example, relay trays may be loaded at pharmacy 101 with medications and other items expected to be needed at various workstations around the facility. The loaded relay trays may be delivered to the workstations by a pharmacy technician or other intra-facility delivery, and may be swapped for "used" relay trays previously delivered to the workstations. The used relay trays can be returned to pharmacy 101 so that any unused medications or other items can be restocked or disposed of if necessary, and the relay trays can be reused.

Figure 11:
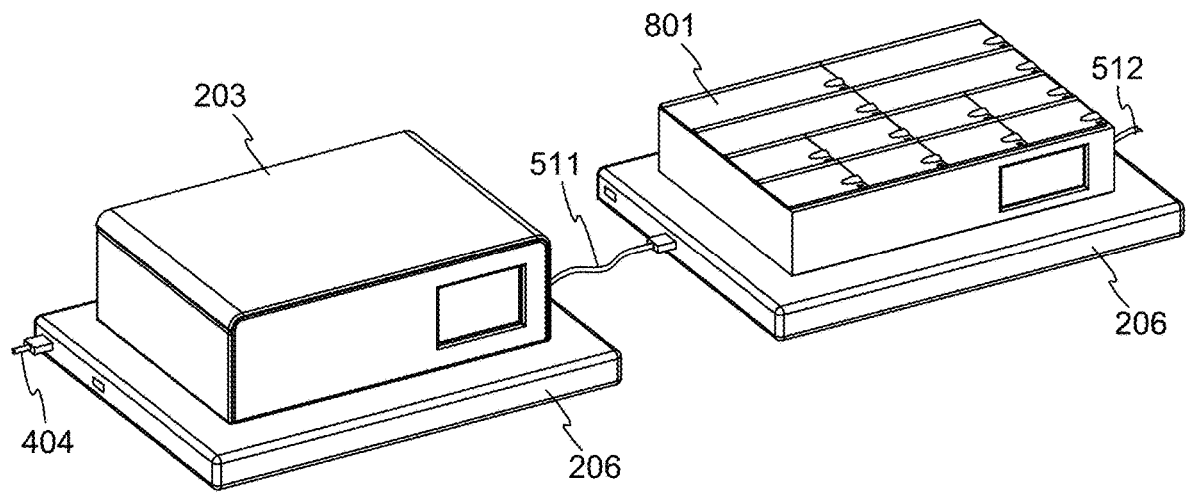
FIG. 11 shows two docking and communication surfaces connected in daisy chain fashion, in accordance with embodiments of the invention.

As was discussed above, docking and communication surfaces in accordance with embodiments of the invention may be connectable together in daisy chain fashion, so that multiple relay trays can receive power and communicate with computer system 106. An example of this arrangement is shown in FIG. 11. In FIG. 11, relay tray 203 is placed on a first docking and communication surface 206, and relay tray 801 is placed on a second docking and communication surface 206. The two docking and communication surfaces 206 are connected together by a cable 511. The first surface in the chain connects with a computer system via cable 404 or another arrangement. Any number of docking and communication surfaces can be daisy chained together, for example via additional cables 512, limited only by the amount of power available in the chain. As is shown in FIG. 11, the relay trays in the chain can be in any mix of types, for example the types exemplified by relay trays 203, 801, and 1001, or other types.

A workstation such as workstations 205 and 207 may include multiple docking and communication surfaces 206, so that the collection of relay trays at any workstation functions in a way similar to cabinet 102 shown in FIG. 1, but without the need for a large cabinet structure. The relay trays may be simply arranged on a work surface, or stored in simple drawers. The relay trays remain powered while stored, so that they are visible to computer system 106 over the network.

Figure 12:
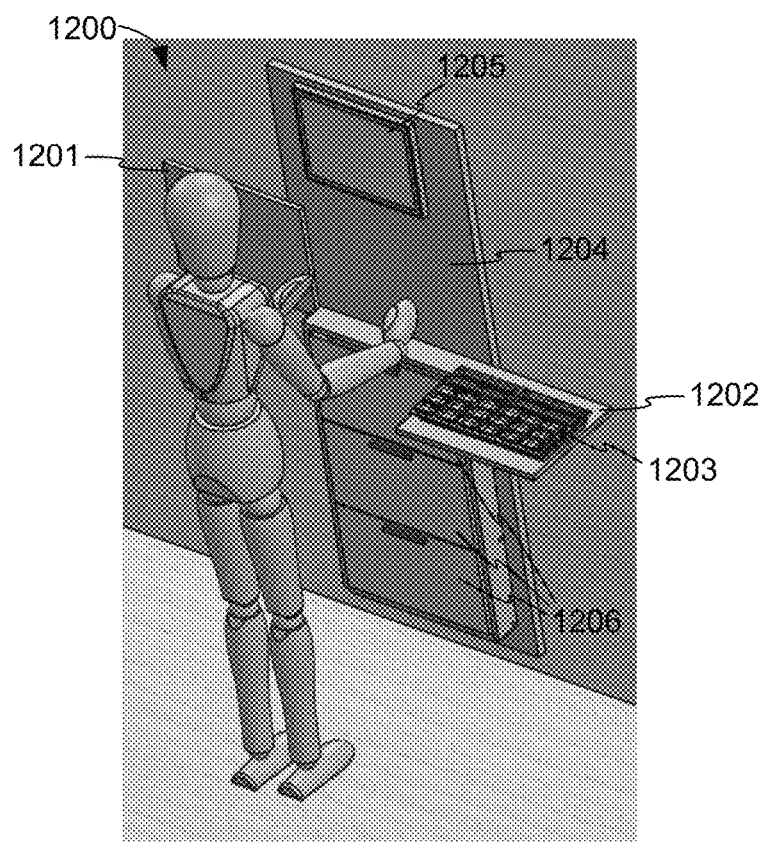
FIG. 12 shows an example wall mounted workstation, in accordance with embodiments of the invention

FIG. 12 shows an example wall mounted workstation 1200, in accordance with embodiments of the invention. Work surfaces 1201 and 1202 may fold up for storage and down for use. Either or both of work surfaces 1201 and 1202 may have a built-in docking and communication surface such as docking and communication surface 206, so that a relay tray 1203 can be place directly on one of the fold-down work surfaces. A computer such as computer 208 may be built in, for example behind panel 1204, and may have a touchscreen display 1205.

Drawers 1206 may also include built-in docking and communication surfaces, so that relay trays stored in drawers 1206 remain powered while stored. Thus, computer system 106 can query any relay tray stored in drawers 1206. When a medication is to be retrieved from one of the relay trays, the user can unlock the appropriate drawer 1206 and move the relay tray to a work surface such as work surface 1202, where the medication can be accessed. Any docking and communication surfaces in work surfaces 1201 and 1202 and drawers 1206 may be connected in daisy chain fashion, or may be separately connected to a power source and to a computer system. A workstation such as workstation may have the advantages that it takes up very little space in a patient room, and allows management of patient medications with added flexibility and lower cost than in some other arrangements.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. It is to be understood that any workable combination of the elements and features disclosed herein is also considered to be disclosed.

The invention has now been described in detail for the purposes of clarity and understanding. However, those skilled in the art will appreciate that certain changes and modifications may be practiced within the scope of the appended claims.

What is claimed is:

1. A relay tray for securely transporting items, the relay tray comprising:
    a lockable transportable container for holding one or more items to be transported;
    an electronic controller including a processor;
    a power interface though which the relay tray can receive electric power;
    a communications interface through which the controller can communicate electronically; and
    a mechanism operable under control of the controller to make items in the lockable transportable container accessible in response to communications received via the communications interface, the mechanism operable by the controller only when power is being received through the power interface from a source external to the lockable transportable container;
    wherein the mechanism is a lock operable by the controller to unlock a compartment of the relay tray;
    and wherein the power interface comprises:
        four electrical contacts on an outside surface of the lockable transportable container for receiving electric power connections; and
        a rectifier that receives power from the four electrical contacts and produces voltage of a polarity suitable for powering the controller.

2. The relay tray for securely transporting items of claim 1, wherein the controller further comprises a nonvolatile memory storing a listing of an item or items in the relay tray.

3. The relay tray for securely transporting items of claim 1, further comprising a plurality of compartments within the lockable transportable container, wherein the compartments are individually lockable, and are individually openable under control of the controller in response to communications received via the communications interface.

4. The relay tray for securely transporting items of claim 3, further comprising a plurality of lights associated respectively with at least some of the compartments, the lights being individually operable under control of the controller.

5. The relay tray for securely transporting items of claim 1, wherein the power interface also serves as the communications interface, with the same electrical contacts carrying both power and communications signals, and wherein the controller is configured to extract incoming communications signals from the electrical contacts of the power interface, and to impose outgoing communications signals on the electrical contacts of the power interface.

6. The relay tray for securely transporting items of claim 1, wherein the communications interface is a short range wireless communications interface.

7. The relay tray for securely transporting items of claim 1, wherein the communications interface is a wired communications interface.

8. The relay tray for securely transporting items of claim 1, wherein:
    the relay tray includes one or more electromechanical actuators; and
    the relay tray does not include a battery powering operation of any of the one or more electromechanical actuators.

9. The relay tray for securely transporting items of claim 1, wherein the relay tray is also openable by a key.

10. The relay tray for securely transporting items of claim 1, further comprising a nonvolatile display on an outside surface of the lockable transportable container.

11. The relay tray for securely transporting items of claim 10, wherein the relay tray stores a hashed identifier of a person for whom an item in the relay tray is intended.

12. The relay tray for securely transporting items of claim 1, further comprising a passive externally-excitable memory device storing an identifier of the relay tray.

13. The relay tray for securely transporting items of claim 1, wherein the controller is configured to authenticate the source of the communications received via the communications interface before making an item in the lockable transportable container accessible.

14. The relay tray for securely transporting items of claim 1, further comprising a low power wireless beacon receiver, and wherein during transport of the relay tray, the controller records the detection of any beacon signals detected by the low power wireless beacon receiver.

15. A relay tray for securely transporting items, the relay tray comprising:
- a lockable transportable container for holding one or more items to be transported;
- an electronic controller including a processor;
- a power interface though which the relay tray can receive electric power;
- a communications interface through which the controller can communicate electronically; and
- a mechanism operable under control of the controller to make items in the lockable transportable container accessible in response to communications received via the communications interface, the mechanism operable by the controller only when power is being received through the power interface;
- wherein the power interface comprises:
  - four electrical contacts on an outside surface of the lockable transportable container for receiving electric power connections; and
  - a rectifier that receives power from the four electrical contacts and produces voltage of a polarity suitable for powering the controller.

16. The relay tray for securely transporting items of claim 15, wherein the four contacts are positioned at the vertices and center of an equilateral triangle.

17. The relay tray for securely transporting items of claim 15, wherein the four contacts also serve as the communications interface, and wherein the controller is configured to extract communications signals imposed on the contacts in addition to the power voltage.

18. The relay tray for securely transporting items of claim 15, wherein the relay tray is configured to receive DC power, and wherein the rectifier produces DC voltage of a polarity suitable for powering the controller.

19. The relay tray for securely transporting items of claim 15, wherein the relay tray is configured to receive AC power, and wherein the rectifier produces rectified AC voltage.

20. A relay tray for securely transporting items, the relay tray comprising:
- a lockable transportable container for holding one or more items to be transported;
- an electronic controller including a processor;
- a power interface though which the relay tray can receive electric power;
- a communications interface through which the controller can communicate electronically; and
- a mechanism operable under control of the controller to make items in the lockable transportable container accessible in response to communications received via the communications interface, the mechanism operable by the controller only when power is being received through the power interface;
- wherein the mechanism comprises a plurality of electromechanical dispensing mechanisms configured to dispense items under control of the controller.

21. The relay tray for securely transporting items of claim 20, wherein items are dispensed in response to communications received via the communications interface.

22. A system for securely transporting medications or other items, the system comprising:
- a central computer system;
- a plurality of relay trays, each relay tray further comprising a lockable transportable container for holding items to be transported, an electronic controller including a processor and non-volatile memory, a power interface though which the relay tray can receive electric power, a communications interface through which the controller can communicate electronically, and a mechanism operable under control of the controller to make items in the lockable transportable container accessible in response to communications received via the communications interface, the mechanism operable by the controller only when power is being received through the power interface, wherein the mechanism is a lock operable by the controller to unlock a compartment of the relay tray, and wherein the power interface comprises four electrical contacts on an outside surface of the lockable transportable container for receiving electric power connections, and a rectifier that receives power from the four electrical contacts and produces voltage of a polarity suitable for powering the controller; and
- a plurality of charging and communications stations in dispersed locations, each of the plurality of charging and communications stations including a power interface for supplying power to one of the relay trays at the station, and a first communications interface for communication with the relay tray at the station, and a second communications interface for communication with the central computer system.

23. The system of claim 22, further comprising an electronic network over which the central computer system communicates instructions to authorize access to the interiors of the lockable transportable containers.

24. The system of claim 22, wherein the power interfaces of the relay trays and the charging and communications stations also serve as the communications interfaces of the relay trays and the first communications interfaces of the charging and communications stations, wherein the same electrical contacts carry both power and communications signals.

25. The system of claim 22, wherein the central computer system maintains an inventory of any medications stored in the plurality of relay trays.

26. The system of claim 25, wherein the central computer system maintains an inventory of any controlled substances stored in the plurality of relay trays.

27. A system for securely transporting medications or other items, the system comprising:
- a central computer system;
- a plurality of relay trays, each relay tray further comprising a lockable transportable container for holding items to be transported, an electronic controller including a processor and non-volatile memory, a power interface though which the relay tray can receive electric power, a communications interface through which the controller can communicate electronically, and a mechanism operable under control of the controller to make items in the lockable transportable container accessible in response to communications received via the communications interface, the mechanism operable by the controller only when power is being received through the power interface; and
- a plurality of charging and communications stations in dispersed locations, each of the plurality of charging and communications stations including a power interface for supplying power to one of the relay trays at the station, and a first communications interface for communication with the relay tray at the station, and a second communications interface for communication with the central computer system;
- wherein the power interfaces of the relay trays and the charging and communications stations also serve as the communications interfaces of the relay trays and the first communications interfaces of the charging and communications stations;

and wherein each of the charging and communications stations comprises:
- a plurality of first linear electrical conductors with exposed metal surfaces, the first linear electrical conductors being connected to each other and held at a first voltage; and
- a plurality of second linear electrical conductors with exposed metal surfaces, the second linear electrical conductors being connected to each other and held at a second voltage different from the first;
- wherein the first and second linear electrical conductors are disposed in alternating arrangement to form a flat surface, and wherein adjacent conductors are spaced apart from each other.

28. A method of transporting an item, the method comprising:
connecting, at a first workstation, a first source of power to a power interface of a relay tray, wherein the relay tray comprises a lockable transportable container for holding items to be transported, an electronic controller including a processor and non-volatile memory, the power interface, a communications interface through which the controller can communicate electronically, and a mechanism operable under control of the controller to make items in the lockable transportable container accessible in response to communications received via the communications interface, wherein the mechanism is operable by the controller only when power is being received through the power interface, and wherein the mechanism is a lock operable by the controller to unlock a compartment of the relay tray;
placing the item to be transported into the relay tray;
locking the relay tray;
storing, in the relay tray, a hashed identifier of a person for whom an item in the relay tray is intended, the hashed identifier being unique to the person and not human-readable, the hashed identifier being generated using a hashing algorithm;
disconnecting the relay tray from the first source of power;
transporting the relay tray containing the item to a second workstation;
connecting, at the second workstation, a second source of power to the power interface of a relay tray;
hashing, at the second workstation, using the hashing algorithm, the name of a person for whom an item is expected to be received in the relay tray;
comparing the hashed name with the hashed identifier stored in the relay tray; and
sending, at the second workstation, to the relay tray via the communications interface an instruction to make the item accessible;
wherein the power interface of the relay tray comprises:
- four electrical contacts on an outside surface of the lockable transportable container for receiving electric power connections; and
- a rectifier that receives power from the four electrical contacts and produces voltage of a polarity suitable for powering the controller.

29. The method of claim 28, wherein connecting the relay tray to the first or second source of power comprises placing the relay tray on a charging and communications surface such that contacts on the relay tray come into contact with conductors in the charging and communications surface to supply power to the relay tray.

30. The method of claim 29, further comprising causing electronic communications to occur between the relay tray and the charging and communications surface via communications signals imposed onto conductors of the charging and communications surface, such that the power interface of the relay tray also functions as the communications interface of the relay tray and the same conductors carry both power and communications signals.

* * * * *

UNITED STATES PATENT AND TRADEMARK OFFICE
CERTIFICATE OF CORRECTION

PATENT NO. : 10,806,676 B2
APPLICATION NO. : 15/884073
DATED : October 20, 2020
INVENTOR(S) : Herbert Fisher It is certified that error appears in the above-identified patent and that said Letters Patent is hereby corrected as shown below:

On the Title Page

Item (57), in the Abstract, Line 5:
Delete "commination" and insert -- communication --, therefor.

Page 2, item (56), References Cited Line 3:
Delete "/20151108213536/" and insert -- /20151106213536/ --, therefor.

In the Specification

Column 1, Line 49:
Delete "nonvolatile" and insert -- non-volatile --, therefor.

Column 4, Line 39:
Delete "invention" and insert -- invention. --, therefor.

Column 5, Line 5:
Delete "al," and insert -- al., --, therefor.

Column 6, Line 65:
Delete "nonvolatile" and insert -- non-volatile --, therefor.

Column 7, Line 1:
Delete "nonvolatile" and insert -- non-volatile --, therefor.

Signed and Sealed this
Eleventh Day of May, 2021

Drew Hirshfeld
*Performing the Functions and Duties of the*
*Under Secretary of Commerce for Intellectual Property and*
*Director of the United States Patent and Trademark Office*